United States Patent [19]

Sorkin et al.

[11] Patent Number: 4,856,534

[45] Date of Patent: Aug. 15, 1989

[54] CONDOM

[76] Inventors: Reubin Sorkin; Larry Sorkin, both of 4721 University Dr., Coral Gables, Fla. 33146

[21] Appl. No.: 110,152

[22] Filed: Oct. 19, 1987

[51] Int. Cl.$^4$ ............................................. A61F 5/44
[52] U.S. Cl. ..................................... 128/844; 604/352
[58] Field of Search ............... 128/132 R, 127, 842, 128/844; 604/228, 229, 349–353

[56] References Cited

U.S. PATENT DOCUMENTS

| | | | |
|---|---|---|---|
| 249,032 | 11/1881 | Ford | 24/495 |
| 1,389,531 | 8/1921 | Riche | 604/351 |
| 2,326,159 | 8/1943 | Mandel | 604/349 |
| 2,548,149 | 4/1951 | Fowler | 604/347 |
| 2,569,931 | 10/1951 | Hora | 24/495 |
| 3,340,876 | 9/1967 | Hill | 604/352 |
| 3,526,227 | 9/1970 | Appelbaum | 604/350 |
| 3,869,762 | 3/1975 | Barrett et al. | 604/352 |
| 4,269,148 | 5/1981 | Holley-Donawa | 604/353 |
| 4,415,548 | 11/1983 | Reddy | 128/132 R |
| 4,498,466 | 2/1985 | Pomeranz | 604/347 |
| 4,568,340 | 2/1986 | Giacalone | 604/353 |
| 4,638,790 | 1/1987 | Conway et al. | 604/352 |
| 4,664,104 | 5/1987 | Jaicks | 604/353 |

FOREIGN PATENT DOCUMENTS

| | | | |
|---|---|---|---|
| 1158507 | 12/1983 | Canada | 604/349 |
| 267218 | 11/1913 | Fed. Rep. of Germany | 604/349 |

Primary Examiner—C. Fred Rosenbaum
Assistant Examiner—Mark O. Polutta
Attorney, Agent, or Firm—John C. Malloy

[57] ABSTRACT

An improved condom which includes a thin-walled, elongated, resilient tubular condom of rubbery impervious material which is sized to jacket the penis of a wearer and a public shield to overlay the public area of a wearer about the penis and structure on the proximal end zone of the condom and on the neck about a central opening on the public shield to accommodate labyrinth type sealing between the proximal end of the condom and the shield to prevent exposure during sexual intercourse and wherein the shield, on its inner surface confronting the wearer is provided with an adhesive means for releasably attaching the shield to the public area surface.

6 Claims, 2 Drawing Sheets

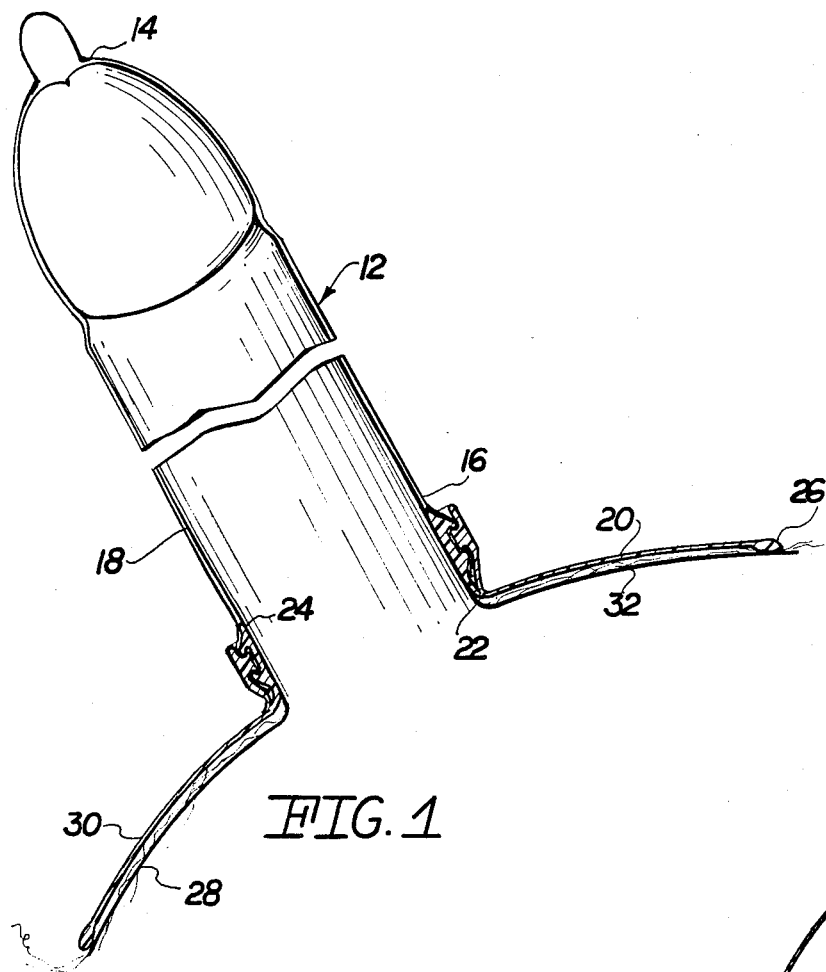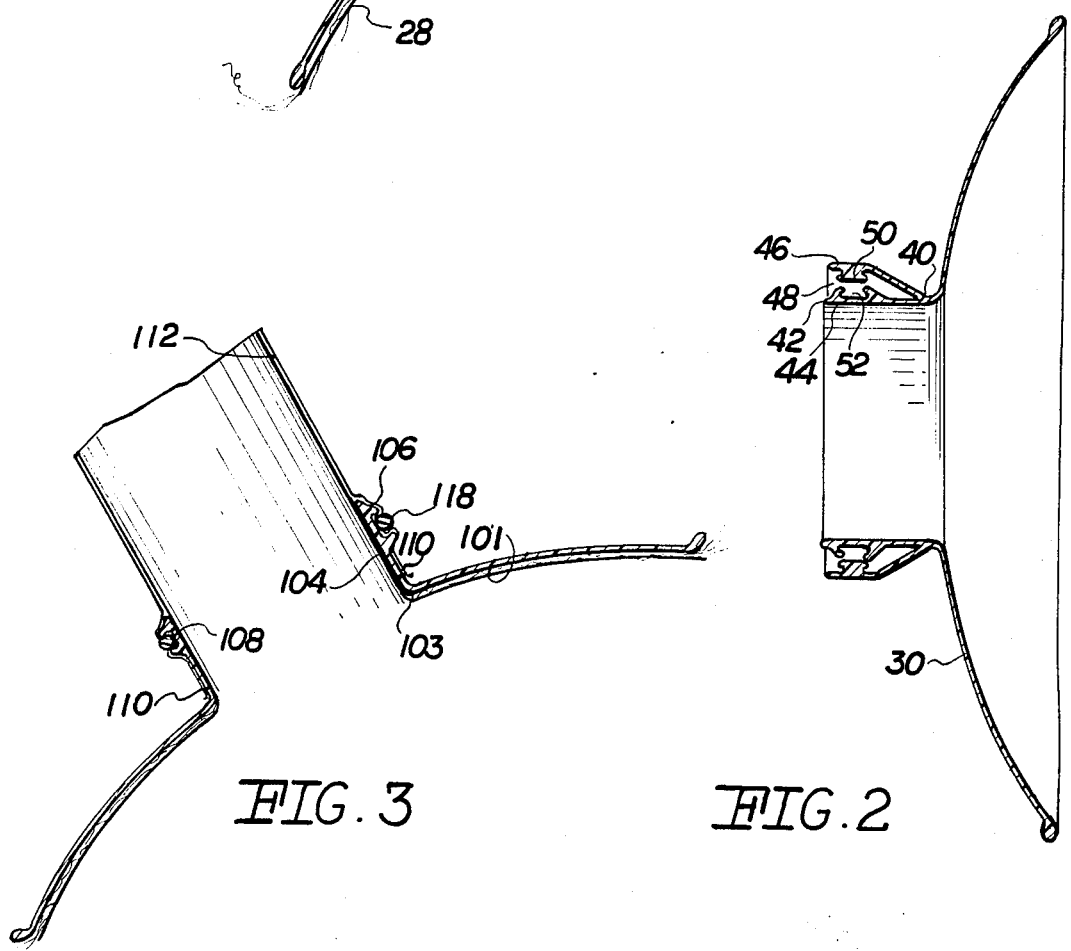

CONDOM

FIELD OF THE INVENTION

This invention relates to condoms and, generally, to an improved condom wherein the condom is provided with a pubic shield to overlay the pubic area of a wearer about the proximal end of a penis and wherein the shield includes adhesives to temporarily secure the pubic shield in position.

BACKGROUND OF THE INVENTION

Generally, condoms have been known in the past and developed so as to be a safe, effective and reliable method of birth control and to provide protection for both men and women from sexually transmitted diseases. It is this latter aspect to which this invention is directed. This invention is of a condom which also includes a mating shield to overlay the pubic area and means to interconnect the proximal end zone of the tubular condom portion about the opening in the pubic shield so as to provide protection against a broad range of sexually transmitted diseases, such as Gonorrhea, Syphilis, AIDS and also other infections such as Herpes and Chlamydia.

Generally the shield is constructed to aid in improving the effectiveness of the normal condom by offering a wider barrier, and insuring that the condom does not slip off during intercourse. The invention is disclosed in three embodiments which are constructed in a way similar to the common diaphragm. The material and size are about the same, with a thin membrane in the middle and a circular ring of latex around the outside edge to hold rigidity and shape. The shield obviously differs from a common diaphragm structure by including, at the center of the shield, a circular opening and an outwardly projecting neck. The function of the latter being to provide in part, means to hold the proximal end of the condom in telescoped relation with the neck and to the penis and the shield. This neck extends less than an inch from the shield and does not interfere with sensitivity during intercourse. In the three embodiments shown, the neck is sized so as to snugly, and rather tightly, jacket the proximal end of the penis of a wearer to ensure that the shield does not slip. It is not so tight, however, as to be unnecessarily constricting. The disclosed embodiments may be commercially provided in several sizes and in general, the neck is of denser latex then the body of the shield.

SUMMARY OF THE INVENTION

The present invention is provided in three embodiments:

The first embodiment includes the shield being constructed with a bifurcated distal end zone of the neck. In use, the shield is first put on and the outer flap formed by the bifurcated distal end of the neck is folded back. Thereafter, the proximal end of the condom is rolled on to an inner flap of the bifurcated distal end of the neck and rolled over it. The top flap is then folded over the base flap or inner flap with the condom locked in place in sandwiched relation between the bifurcated distal end of the neck. The condom is locked in place by pressing the closure together around the neck so that a male rib and a female groove close and captivate the proximal end zone of the condom in a manner similar to the labyrinth sealing means of the commercially available "Zip Lock" bag. In embodiment two the shield differs from the first embodiment in that the neck of the shield is not bifurcated and, an O-ring is provided to be slipped over the neck when in telescoped relation with the proximal end of the condom so that when the O-ring is slipped over the penis it will dwell in a groove provided in the exterior surface of the neck of the shield. In embodiment number three the shield is slipped on after the condom is put in place. The shield has a ribbed neck that is tight enough to ensure that the condom does not slip off and it snugly jackets the exterior surface of the tubular condom at the proximal end zone again providing a labyrinth type seal.

DESCRIPTION OF THE PRIOR ART

U.S. Pat. No. 2,591,783 to Braddock discloses a protecting shield that is strapped onto the hips of a male. The shield covers the entire pubic area of the male and has a hole in the middle of it through which is inserted the penis. A condom is detachably mounted around the edge of the hole on the shield and the penis is inserted into the condom.

U.S. Pat. No. 4,354,495 to Hogin discloses a condom having a retention strap. A retention strap is attached to the proximal terminal edge of the condom at the opening of the tubular portion of the condom. The retaining strap loops below the portion of the condom. The retaining strap loops below the scrotum of the male user.

U.S. Pat. No. 919,875 to Johnson discloses a suspensory that includes a shield that is strapped onto the hips of a male. The shield has a hole in the middle through which passes the penis. A sheath is detachably attached to the edge defining the hole and the penis is disposed in the sheathe. U.S. Pat. No. 1,490,793 to Ajamian, et al. discloses a similar device as that disclosed by the patent to Johnson but the Ajamian, et al. device is utilized for infant males.

U.S. Pat. No. 3,759,254 to Clark discloses a hygienic appliance that includes a condom with an integral, thin wall scrotum sack attached thereto.

OBJECTS OF THE INVENTION

It is an object of the present invention to provide an improved condom with a shield to overlay the pubic area of a user and a labyrinth type sealing means on the proximal end zone of the condom and about an opening in the shield for mutually intercooperation and locking, to maintain the proximal end of the condom together with the shield as a protective barrier for a wearer. It is a general object of the present invention to provide a condom and pubic shield with a means for connecting the two together to form a labyrinth seal at the juncture of the condom and the shield which provides protection, not only for the penis, but also the pubic area of the user.

It is a general object of the present invention provided by the type described which is relatively inexpensive to manufacture, easy to use and which provides protection from disease during intercourse.

FIG. 1, is a longitudinal section of the condom shield with a condom;

FIG. 2, is a longitudinal section of the shield;

FIG. 3, is an alternative embodiment of the shield; and

FIG. 4, is another alternative embodiment.

DESCRIPTION OF THE DRAWINGS

Referring to the drawings, and particularly to FIG. 1, which together with FIG. 2 illustrates the first preferred embodiment of the present invention, it is seen that there is provided a condom generally designated by the numeral 12. As is customary, it is of a thin walled, elongated, resilient tubular member of rubbery and impervious material. It has a closed distal end 14 and an open proximal end zone 16 with an intermediate zone 18 between the distal end and proximal end zone. It is sized to be telescoped over a penis and to jacket it for use. There is also provided a pubic shield 20 which is composed of a relatively thick sheet, relative to the thickness of the condom, and at least about one-sixteenth of an inch in thickness. This shield is about two inches in radius and is preferably circular. It has a central opening 22 bounded by a peripheral edge 24. It is sized to overlay the pubic area of a wearer and the exterior of the shield is preferably bordered by a rigidifying annular enlarged rib 26. The central opening is sized for passage of the penis of a wearer and as seen the shield has an inner surface 28 and an outer surface 30. Means are provided on the inner surface to adhere to the pubic area of a wearer when in covering relation thereof. This means is designated by the numeral 32. It may be an adhesive means but preferably this means is of a Unibase Ointment, that is a greaseless, water suspended, non-oily lubricant such as is available commercially from the Parke-Davis Company and sold under the trademark Unibase Ointment. Preferably, the condom is lubricated both exteriorly and interiorly by a water base lubricant and the lubricant is of the type known commercially as the K.Y. Jelly manufactured and distributed by the Johnson and Johnson Company. The adhesive means provides that the shield is held in place by the adherence of the inner surface ot the pubic area of a wearer and does not separate in use from the condom or when the penis becomes flaccid after intercourse.

With continuing reference to the first preferred embodiment of FIG. 2, it is seen that the shield is provided with a neck 40 extending from the outer surface 30 about the opening 22. The distal end 42 of the neck is bifurcated, providing an inner flap 44 and an outer flap 46 with a groove 48 between the flaps. The confronting surfaces of the flaps are provided with a male member 50 formed on one of the flaps, and a female recess 52 formed or the other of the flaps. This provides a mutually intercooperating means on the distal end zone of the neck disposed and structural to cooperate with the proximal end zone of the condom to provide a labyrinth seal and interconnection between the proximal end zone of the condom and the distal end of the neck. In use, the top of the outer flap 46 is rolled back upon itself. The distal end zone of the condom is positioned between the flaps provided by the bifurcated end, and, thereafter, the outer flap is positioned over the inner flap with the proximal end of the condom sandwiched therebetween. The condom is captivated by pressing the male member into the female member in locking engagement similar to the structure provided in conventional, commercially available "Zip Lock" bags.

Figure 4:
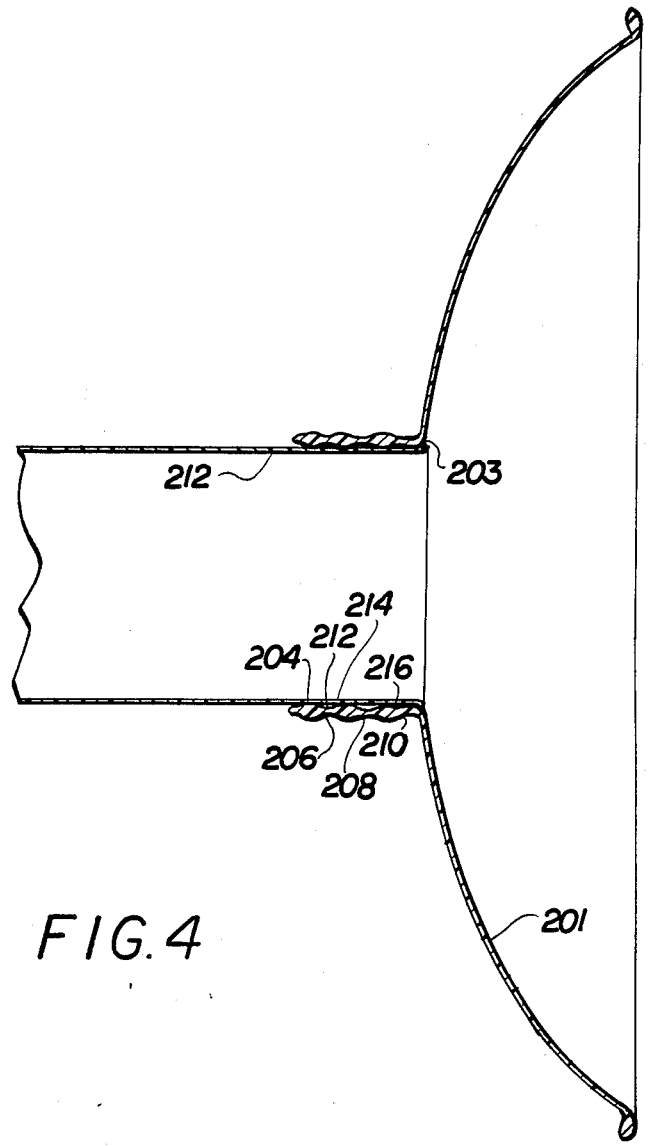

Referring now to the embodiment shown in FIG. 3, it is seen that the shield designated by the numeral 101 is provided again with a central opening 103 from which there extends a neck 104. On the exterior surface 106 of this neck there is provided an annular groove 108. The proximal end zone 110 of the condom 112 is positioned in telescoping relation over the neck and an O-ring 118 is provided which is sized for receipt snugly within the annular groove with the proximal end zone of the condom being captivated in the groove by the O-ring. To this end, the groove may have a slightly smaller opening then the diameter of the O-ring so that the O-ring is compressed and deformed slightly when being applied.

With reference to the embodiments shown in FIG. 4, there is again shown a pubic shield 201 with an opening 203 from which there extends a neck 204. As seen, the neck is ribbed providing a plurality of grooves 206, 208 and 210 exteriorly and interiorly 212, 214 and 216. The proximal end zone 212 of the condom is jacketed by the neck 204 with the ribbed surfaces, providing a labyrinth and tight seal at the base of the penis. Preferably, in this embodiment, the shield 201 is applied after the condom 212. However, in the event that the shield 201 is applied first and the condom 212 overlays and jackets the neck 204, the proximal end zone of the condom 212 will be held snugly in place and against the penis by the snug proximal end base jacketing of the neck 204 about the penis.

While the instant invention has been shown in three practical and preferred embodiments, it will be recognized that in each embodiment, there is a shield provided with a central opening and adhesive means to apply it and maintain it in position during intercourse and wherein the shield includes a neck about the opening which extends outwardly and telescopes with the proximal end of the condom so that mutually intercooperating means may be utilized to provide a labyrinth seal at the proximal end of the condom, that is about the base of the penis, and, also, protection is provided for the pubic area.

What is claimed is:

1. A condom device comprising:
   (a) a thin-walled, elongated, resilient condom of rubbery impervious material having a closed distal end, an open proximal end zone, an intermediate zone between the end and the end zone, said tubular condom being sized to receive and jacket the penis of a wearer,
   (b) a protective pubic shield comprising a relatively thick sheet relative to the condom wall thickness and being sized to overlie the pubic area of the wearer, said shield having a central opening bounded by a peripheral edge and being sized for passage therethrough of the penis of the wearer,
   (c) said shield having an inner surface and an outer surface, means on the inner surface to adhere the inner surface to the pubic area of a wearer in covering relation thereof about the penis,
   (d) an intercooperating means formed on the condom about the proximal end zone and on said shield about the opening for attaching the condom to said shield for use,
   (e) said shield including a tubular neck extending from the edge of the opening and sized to receive and jacket a proximal end of the penis of the wearer,
   (f) said neck including a distal portion having a bifurcated configuration at least partially defining said intercooperating means and comprising an annular outer member and an annular inner member both secured to and extending outwardly from said neck in surrounding relation to the distal end of the penis said outer and inner members having confronting surfaces, (g) said outer and innner members spaced from one another along their length and defining an annular groove formed therebetween for receiving said open proximal end zone of the condom, and (h) said intercooperating means further comprising annularly configured intermating male and female members formed on said confronting surfaces of said outer and inner members, said proximal end zone nested within the annular groove in sandwiched relation between said male and female members when interlocked with one another, whereby the proximal end zone is enclosed within the bifurcated neck.

2. The device as set forth in claim 1 wherein the tubular condom is exteriorly provided with water base lubricating means.

3. The device as set forth in claim 1 wherein the condom is interiorly provided with a water based lubricating means.

4. The device as set forth in claim 3 wherein the condom is provided exteriorly with water base lubricating means.

5. The device as set forth in claim 1 wherein said pubic shield is of a sheet of flexible, pliable material.

6. The device as set forth in claim 5 wherein the pubic shield is circular as seen in plan and is of a radius of at least about two inches.

* * * * *